United States Patent [19]

Karl et al.

[11] Patent Number: 5,627,078

[45] Date of Patent: May 6, 1997

[54] MULTIVALENT DEXTRAN REAGENT FOR USE IN PRECIPITATION TESTS

[75] Inventors: Johann Karl, Peissenberg; Josef Maier, Weilheim, both of Germany

[73] Assignee: Boehringer Mannheim GmbH, Mannehim, Germany

[21] Appl. No.: 252,539

[22] Filed: Jun. 1, 1994

Related U.S. Application Data

[63] Continuation of Ser. No. 987,491, Dec. 7, 1992, abandoned.

[30] Foreign Application Priority Data

Dec. 5, 1991 [DE] Germany ............... 41 40 142.5

[51] Int. Cl.$^6$ ............................................. G01N 33/563
[52] U.S. Cl. ............... 436/512; 436/529; 436/536; 436/538; 436/539; 435/7.1; 435/7.5
[58] Field of Search ............................. 436/512, 529, 436/536, 538, 539; 435/7.1, 7.5

[56] References Cited

U.S. PATENT DOCUMENTS

| | | | |
|---|---|---|---|
| 4,434,150 | 2/1984 | Azad et al. | 436/823 |
| 4,468,470 | 8/1984 | Aalberse | 436/534 |
| 4,530,400 | 7/1985 | Marshall | 436/539 |
| 4,530,900 | 7/1985 | Marshall | 435/7 |
| 4,582,810 | 4/1986 | Rosenstein | 436/823 |
| 4,604,365 | 8/1986 | O'Neill et al. | 436/528 |
| 4,615,986 | 10/1986 | Yoshida | 436/500 |
| 4,657,853 | 4/1987 | Freytag et al. | 435/7.9 |
| 4,692,330 | 9/1987 | Ryohei et al. | 436/529 |
| 4,749,647 | 6/1988 | Thomas et al. | 436/539 |
| 4,772,550 | 9/1988 | Greenguist | 436/823 |
| 4,778,751 | 10/1988 | El Shami et al. | 435/7.5 |
| 4,925,648 | 5/1990 | Hansen et al. | 427/85.8 |
| 4,975,532 | 12/1990 | Rowley et al. | 436/524 |
| 5,045,480 | 9/1991 | Johnson et al. | 436/532 |
| 5,057,313 | 10/1991 | Shih et al. | 424/85.91 |
| 5,167,925 | 12/1992 | Carbonell et al. | 436/539 |
| 5,180,815 | 1/1993 | Misuda | 436/823 |
| 5,248,772 | 9/1993 | Siiman et al. | 536/112 |
| 5,268,306 | 12/1993 | Berger et al. | 436/527 |
| 5,350,574 | 9/1994 | Erlanger et gal. | 514/9 |

FOREIGN PATENT DOCUMENTS

| | | |
|---|---|---|
| 0317796 | 5/1981 | European Pat. Off. . |
| 0141620 | 5/1985 | European Pat. Off. . |
| 0079962 | 8/1985 | European Pat. Off. . |
| 0317796 | 5/1989 | European Pat. Off. . |
| 405578 A3 | 5/1991 | European Pat. Off. . |
| 0141620 | 10/1991 | European Pat. Off. . |
| 483512 A1 | 5/1992 | European Pat. Off. . |
| 2601455 | 7/1986 | France . |

OTHER PUBLICATIONS

Wilchek et al. "Avidin–Biotin Technology" in Methods in Enzymology vol. 184, pp. 14–45, 49–57, 518–529 (1990).
Polysciences Inc. Oct. 1990–1991, p. D7.
WO 89/00694 –Coulter Electronics Inc.

*Primary Examiner*—Carol A. Spiegel
*Attorney, Agent, or Firm*—Nikaido, Marmelstein, Murray & Oram LLP

[57] ABSTRACT

The present invention concerns a multivalent dextran reagent for use in a precipitation test for the determination of a specifically bindable substance comprising dextran to which several molecules of a receptor $R_1$ which is capable of specific binding to the substance to be determined or of the specifically bindable substance or of an analogue of this substance are bound or can be bound.

10 Claims, 3 Drawing Sheets

MULTIVALENT DEXTRAN REAGENT FOR USE IN PRECIPITATION TESTS

This application is a continuation of application Ser. No. 07/987,491 filed Dec. 7, 1992, now abandoned.

BACKGROUND OF THE INVENTION

1. Field of the Invention

The invention concerns a multivalent dextran reagent for use in a precipitation test for the determination of a specifically bindable substance comprising dextran to which several molecules of a receptor $R_1$ which is capable of specific binding to the substance to be determined or of the specifically bindable substance or of an analogue of this substance are bound or can be bound.

The invention also concerns a precipitation test for the determination of a specifically bindable substance in which the multivalent dextran reagent is used in addition to reagent which are usually necessary for a precipitation reaction such as buffer, substance for reducing interference, reaction accelerator or detergent.

2. Description of the Prior Art

Very many substances occur in body fluids and tissues which are capable of binding to a specific binding partner and which serve as parameters for particular diseases or for the state of health of the body. These include haptens such as hormones, proteins such as C-reactive protein (CRP), glycated proteins and viral proteins as well as antibodies. When monitoring drug treatment it is often necessary to determine pharmaceutical substances in blood. The bindable substances occur in a wide variety of concentrations in the body fluids or tissues. Various proteins such as IgG, IgA or apolipoproteins occur in high concentrations while for example hormones or drugs or even other proteins may be present in very low concentrations. The detection of these substances can be carried out by a precipitation test. Specifically bindable substances which are at least bivalent, i.e. have at least two epitopes which bind to the receptor in the precipitation test, can be precipitated directly by the addition of a receptor capable of specific binding. In order to increase the sensitivity of the nephelometric or turbidimetric measurement it is often necessary to bind the receptors capable of specific binding to highly polymerized particles e.g. latex or red blood corpuscles. Such detection methods with a turbidimetric evaluation are denoted agglutination tests and have been described in Eur. J. Biochem. 30 (1971), 553–560.

Low-molecular substances, such as e.g. haptens, which only have one epitope to which the specific receptor binds in the precipitation or agglutination test cannot be detected with the direct test procedure for the precipitation or agglutination test since no crosslinking can form which leads to precipitation. An immuno-precipitation test is known from EP-A-0 079 962 which utilizes a competitive test procedure in which the solution containing the haptens to be determined is brought into contact with an albumin coated with hapten. Addition of antibodies capable of binding to the haptens leads to a precipitation reaction. Since the hapten bound to the albumin competes with the hapten present in the sample, the precipitation reaction is smaller the more hapten is present in the sample. Other proteins are described as hapten carriers in the state of the art e.g. IgG, latex particles or synthetic polymers such as e.g. polyaspartate (EP-A-0 317 796).

All these agglutination tests or precipitation tests still have some considerable disadvantages. Pure precipitation tests have a sensitivity which is too low for some parameters. Therefore specific receptors are bound to latex particles in order to increase the sensitivity of agglutination tests. The coupling can, on the one hand, lead to an impairment of the reactivity of the receptor itself and, on the other hand, the addition of reaction accelerators such as e.g. polyethylene glycol, which has to be added to avoid a long incubation period, can lead to spontaneous agglutination reactions of the latex particles. It is also difficult to exactly control the number of receptors coupled to the individual latex particles. As a consequence considerable variations can occur between the individual lots. Binding of unspecific factors from the sample to the surface of the latex particles can lead to inaccuracies in the measurement.

Difficulties can also occur when using carrier-bound haptens such as hapten-albumin or hapten-IgG. Possible interfering factors are anti-IgG and anti-albumin antibodies in the serum. Also in this case it is difficult to exactly control the number of haptens on the individual molecules in particular when using natural molecules such as proteins. Moreover these materials are not stable on storage to an extent which would allow their unlimited use. These materials are not optimal with regard to their solubility properties and their tendency to denature and cannot therefore be used universally.

Up to now it has been necessary depending on the test procedure, whereby one has to differentiate between a direct or competitive test procedure, on the substance to be detected such as haptens, antigens or antibodies and on the concentration of the substance to be detected to test which of the possible materials available is the optimal carrier material in each case for binding the specific receptor or the specifically bindable substance for an agglutination test or a precipitation test with carrier-bound haptens. A carrier material which can be used universally for all test variants, all substances to be detected and concentrations and which in addition has a long shelf-life, good solubility properties and a low tendency to denature, and which also allows the use of different molecular sizes and a wide range of incorporation rates is not known up to now.

SUMMARY OF THE INVENTION

The object of the present invention was therefore to provide a carrier material for universal use in direct or competitive precipitation tests which allows the detection of substances which have one or several binding sites with a high sensitivity, accuracy and stability and does not have the aforementioned disadvantages.

The object is achieved by the invention which is characterized in more detail in the claims. This object is achieved essentially by a multivalent dextran reagent for use in a precipitation test for the determination of a specifically bindable substance comprising dextran, to which several molecules of a receptor $R_1$ which is capable of specific binding to the substance to be determined or of the specifically bindable substance or of an analogue of this substance are bound or can be bound.

The multivalent dextran reagent can be used in a precipitation test for the determination of a specifically bindable substance.

The invention also concerns a precipitation test as well as a test kit for the determination of a specifically bindable substance which contains or uses the multivalent dextran reagent in addition to further auxiliary agents or additives which are necessary for the method.

DESCRIPTION OF THE PREFERRED EMBODIMENTS

Figure 1:
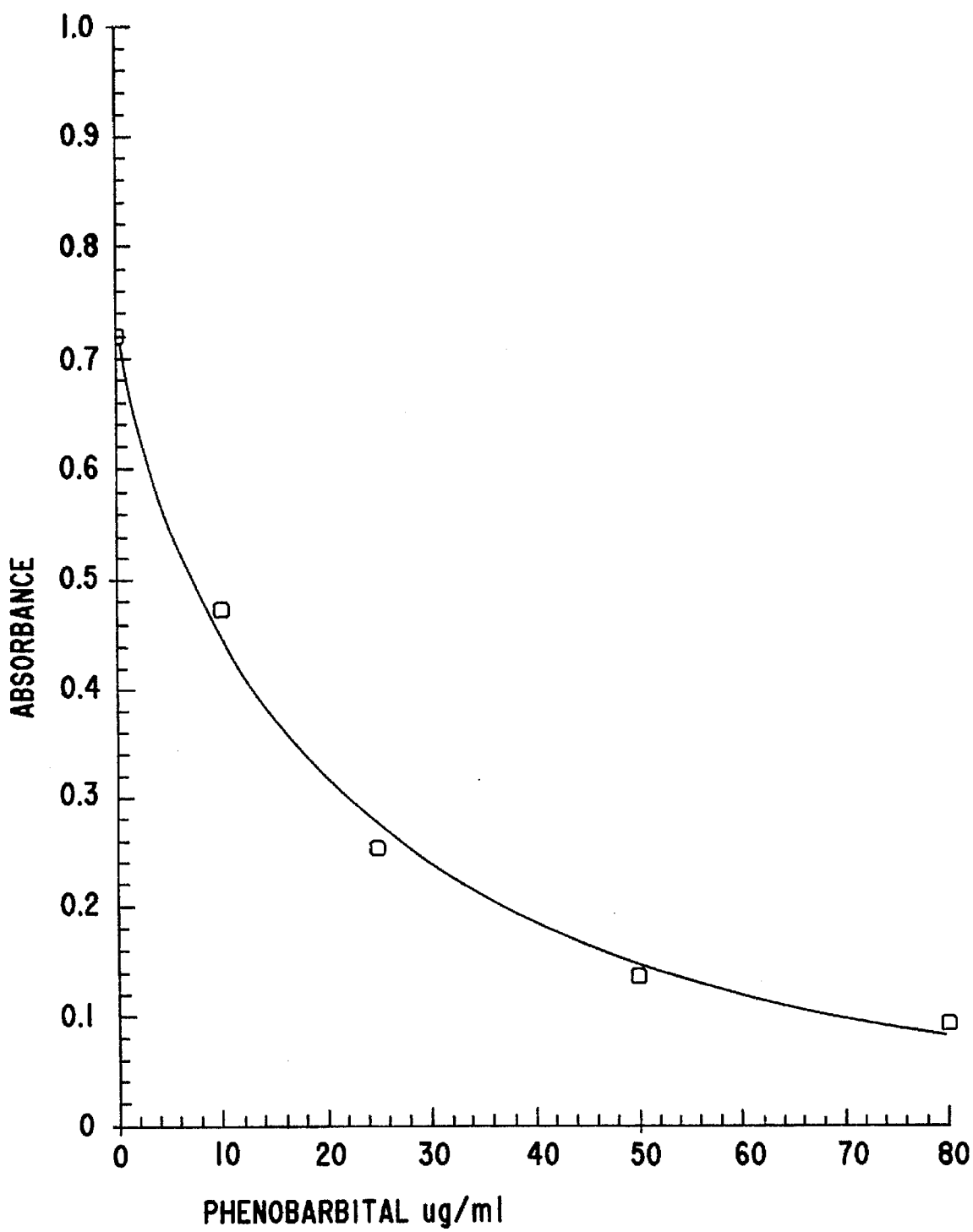
FIG. 1 shows the competitive detection of PHEBA.

The precipitation test containing the multivalent dextran reagent is suitable for the determination of many substances which are to be determined in body fluids or tissue extracts and are capable of a specific binding wherein substances in low concentrations can be detected equally as well as highly concentrated substances. Monovalent as well as polyvalent substances can be determined. The multivalent dextran reagent is preferably used for the determination of monovalent substances. Since antibodies which are directed against the multivalent dextran reagent should not occur in serum, no antibody interference which could be attributed to this occurs in the test when using the dextran reagent.

In this connection a substance is denoted monovalent which has only one binding site for a specific partner. Examples of this are haptens, e.g. hormones, peptides such as glycated haemoglobin ($HbA_1$) and pharmaceutical agents. A substance is denoted polyvalent when it has at least two binding sites for the specifically bindable binding partner such as e.g. proteins such as CRP and α-1 microglobulin, glycated proteins such as glycated albumin and glycated IgG, antigens and antibodies such as IgG, rheumatoid factor (RF) or antistreptolysin O (ASLO).

For this a multivalent dextran reagent to which either a receptor $R_1$ which is capable of specific binding to the substance to be detected or the specifically bindable substance or an analogue of this substance is bound or can be bound is added to the sample solution. A multivalent dextran reagent is understood as dextran molecules to which several molecules of the receptor $R_1$ or of the specifically bindable substance or of the analogue of this substance are bound or can be bound. In addition further reagents necessary for a precipitation test such as buffer, reaction accelerator, substance which reduces interference, detergents and others are added to the test mixture whereby the addition of these reagents to the sample does not necessarily have to occur at the same time as that of the dextran reagent.

A variety of reaction principles is possible which can be carried out with the method which uses the multivalent dextran reagent according to the present invention.

Variant 1 serves to detect bivalent or polyvalent substances which have at least two binding sites for the receptor $R_1$ capable of specific binding to these substances. It utilizes a direct test procedure in which a multivalent dextran reagent is used composed of dextran to which several molecules of a receptor $R_1$, which is capable of specific binding to the substance to be determined, are bound. The extent of the precipitation reaction is directly proportional to the substance to be determined in the sample.

Variant 2 also serves to detect polyvalent substances in which the direct test procedure is also utilized. In this case receptor $R_1$, which is capable of specific binding to the substance to be determined, is not bound directly to dextran but is bound via two receptors $R_3$ and $R_4$ which are capable of binding to one another. $R_3$ in this case is bound to the dextran molecule and $R_4$ is bound to $R_1$.

Monovalent substances such as haptens, short peptides or pharmaceutical agents are preferably detected with the third variant. The principle corresponds to that of a competitive precipitation test. In this case the multivalent dextran reagent comprises dextran to which the specifically bindable substance or an analogue of this substance is bound. A receptor $R_2$ which is at least bivalent and capable of specific binding to the substance to be determined is added to the test mixture. When the sample solution is incubated with the multivalent dextran reagent and $R_2$, the substance to be determined in the sample competes with the multivalent dextran reagent for binding to $R_2$. The extent of the precipitation is inversely proportional to the substance to be detected in the sample.

Variant 4 corresponds in principle to variant 3 except that the specifically binding substance or an analogue of this substance is not bound directly to dextran but instead can be bound via the receptors $R_3$ and $R_4$ whereby $R_3$ is bound to the dextran molecule and $R_4$ is bound to the specifically bindable substance or an analogue of this substance.

The advantage of using receptors $R_3$ and $R_4$ in the test variants 2 and 4 is that the dextran molecule to which the receptor $R_3$ is coupled can be used universally for several parameters to be detected.

The use of the multivalent dextran reagent according to the present invention in direct or competitive precipitation tests increases the sensitivity of the detection of the specifically bindable substance compared to conventional precipitation tests. An increase in the sensitivity by the use of particles such as e.g. latex particles usually appears to be no longer necessary.

Certain parameters in low concentrations require a very low detection limit e.g. pharmaceutical agents in low dosages. The sensitivity of the competitive precipitation test according to the present invention—variants 3 and 4 described above—can be increased even further in the embodiment denoted test variant 5 wherein in addition to the multivalent dextran reagent comprising dextran to which several molecules of the specifically bindable substance or of an analogue of this substance are bound or can be bound, a receptor $R_2$ is used of which several molecules are likewise bound to dextran. In this case it is necessary to exactly control the coupling of the dextran reagents with the specifically bindable substance and the receptor $R_2$ and to match one against the other. The multivalent dextran reagent according to the present invention provides excellent conditions for this since the coupling can be controlled very exactly. Thus in test variant 5 two multivalent dextran reagents are used which are together capable of a precipitation reaction. This precipitation reaction is reduced by addition of the substance to be determined.

Thus there are several methods of carrying out the precipitation test defined according to the present invention. The substance to be determined can be any substance which is capable of specific binding and in particular—as defined above—a hapten, a monovalent, bivalent or polyvalent antigen or an antibody.

The basic framework of the dextran reagent is the polysaccharide dextran. This can be used in different degrees of high polymerization. Dextran with a molecular weight of 10000 up to the solubility limit which is at about 2 million has proven to be particularly suitable. Dextran is preferably used with a molecular weight of 20000 to 500000. The precipitation test according to the present invention has the highest sensitivity within these preferred limits.

The term "multivalent dextran reagent" means that several molecules of the receptor $R_1$ or of the specifically bindable substance or of its analogue are bound or can be bound to a dextran molecule. The ratio of dextran: bound molecules is denoted coupling. A coupling of 1:2 to 1:50 has proven to be suitable. Couplings of 1:5 to 1:40 are particularly suitable. When the coupling of the dextran molecules is even denser interference by steric effects can occur. The incorporation rate must be optimized within the said limits for each particular bindable substance. Depending on the concentration of the bindable substance to be detected in the sample, different rates of incorporation within the said limits are advantageous. Compared to the carrier molecules which have been usually used up to now in the state of the art, such as BSA and IgG, it turns out that the coupling using the dextran reagent can be higher. This results in an increase in the sensitivity of the test.

A molecule is selected as receptor $R_1$ which is capable of specific binding to the substance to be determined. The receptor $R_1$ and the substance to be determined thus constitute a binding pair. $R_1$ has to have at least one binding site, but can, however, also have two or several binding sites for the substance to be determined. Since several receptors are bound or can be bound to the dextran reagent, a receptor $R_1$ having only one binding site leads to a cross-linking and thus to a precipitation. The receptor $R_1$ is selected according to the substance to be determined in each case. A multitude of receptors are suitable for this. In order to determine antigens, proteins, DNA or sugar it is particularly preferable to use antibodies or antibody fragments such as $F(ab)_2$, Fab or Fab' fragments. In order to determine DNA it is also advantageous to use a complementary DNA as receptor $R_1$. If an antibody or another sample receptor which has at least two binding sites is to be determined in the sample itself then the complementary binding partner such as e.g. hapten, antigen, protein, sugar or also fragments thereof such as e.g. individual epitopes of a protein can be used as the receptor $R_1$.

In the competitive test variant the specifically bindable substance or an analogue of this substance is bound directly to dextran or bound via the receptors $R_3$ and $R_4$. The specifically bindable substance can preferably correspond to the unchanged substance to be determined. It is also possible to use a derivative of the substance to be determined or a part of the substance to be determined such as for example a protein epitope. It is only important that the substance or the derivative or the part is capable of binding to the receptor $R_2$ whereby it is not absolutely necessary that the receptor $R_2$ binds to these bound substances with the same strength as to the substance to be determined which is present in the sample.

All molecules which are capable of specifically binding to the substance to be determined can be used as receptor $R_2$ which is required in addition to the multivalent dextran reagent in the competitive test procedure of test variants 3 and 4. They correspond to receptor $R_1$ except that receptor $R_2$ must have at least two binding sites. Receptors with only one binding site for the specifically bindable substance, such as e.g. Fab or Fab' fragments cannot be used.

In contrast monovalent receptors can be used in addition to bivalent and polyvalent receptors in test variant 5 in which the receptor $R_2$ is used bound to dextran. Thus it is possible to use all receptors that can be used as receptor $R_1$ as described above. Since haptens are preferably detected using the competitive test procedure, specific antibodies or antibody fragments are preferably used as receptors.

In test variants 2 and 4, receptors $R_3$ and $R_4$ which are capable of binding to one another are used to bind the receptor $R_1$ or the specifically bindable substance or the analogue of this substance wherein $R_3$ is bound to dextran and $R_4$ is bound to $R_1$ or to the specifically bindable substance or to the analogue of this substance. Suitable binding pairs $R_3$–$R_4$ are in particular biotin-streptavidin or avidin, hapten-antibody, antigen-antibody, concanavalin-antibody, sugar-lectin, hapten-binding protein, e.g. thyroxine and thyroxine-binding globulin, or oligopeptide-antibody.

Streptavidin or avidin-biotin is preferably used as the binding pair whereby streptavidin or avidin is particularly preferably bound to dextran. Biotin is preferably bound to the receptor $R_1$ or to the specifically bindable substance or to the analogue of this substance. This biotin conjugate is produced according to known methods (e.g. analogous to the European Journal of Biochemistry 131 (1980) 333–338).

The binding of the receptor $R_1$, the specifically bindable substance or of the analogue of this substance or of the receptor $R_3$ to dextran is carried out according to known methods of the state of the art. The coupling can be carried out directly to the hydroxyl groups present on the dextran. For the coupling it is preferred that further functional groups such as amino, carboxyl, sulfhydryl, chloromethyl, hydrazido or diazonium residues are introduced into the dextran molecule.

Amino residues are particularly preferably inserted as functional groups. The receptor $R_1$, the specifically bindable substance or the analogue of this substance or the receptor $R_3$ is coupled to dextran or to functionalized dextran with the aid of coupling reagents as described for example in EP-A-0 317 796. The coupling is regulated by means of the provided stoichiometry and the reaction conditions such as pH, temperature and reaction time.

Further auxiliary agents or additives can for example be additionally contained in the precipitation test according to the present invention e.g. as a reaction accelerator. PEG 6000 at a concentration of 1–5% by weight is usually added as a reaction accelerator. In addition detergents may be present in concentrations between 0.01 and 4% by weight.

The method can be carried out in one or several steps. The evaluation is carried out by measuring the extent of the precipitation. Methods for this are known. A photometric turbidity measurement or the measurement of scattered light by nephelometry is for example suitable for this.

The present invention also concerns a test kit for the determination of specifically bindable substances which, in addition to further auxiliary agents or additives necessary for the precipitation test, contains a multivalent dextran reagent comprising dextran to which several molecules of the receptor $R_1$ which is capable of specific binding to the substance to be determined or of the specifically bindable substance or of an analogue of this substance are bound or can be bound.

In addition to the buffer substances usually used, reaction accelerators at concentrations of 1–5%, detergents at concentrations of 0.01–4% or substances which reduce interference can be present in the test kit as auxiliary agents or additives. The test kits which contain the reagents for the method variants 3 and 4 additionally contain the receptors $R_2$ which are necessary for the precipitation reaction.

The invention is elucidated by the following examples.

EXAMPLE 1

Detection of phenobarbital (PHEBA)

1.1 Production of aminodextran 11.6 g chloroacetic acid, sodium salt is dissolved in 100 ml $H_2O$, added to a solution of 11.2 g dextran with a molecular weight of 40000 in 36 ml 1M NaOH and stirred for 20 hours at 40° C. Afterwards the pH is adjusted to a value of 4 with 1M HCl and concentrated to a volume of 50 ml on a rotary evaporator. The carboxylmethyldextran which forms is dissolved in 50 ml 2M ethylene diamine×2 HCl, pH 5 and 3 g N-ethyl-N'(3-dimethylaminopropyl)carbodiimide×HCl is added in portions within 60 minutes. It is stirred for a further three hours at room temperature at a constant pH value of 4.7 whereby NaOH or HCl is added by means of a titrator. The product is twice dialyzed against desalted $H_2O$ and subsequently lyophilized.

1.2 Production of phenobarbital (PHEBA)-dextran

The hapten phenobarbital is coupled to amino dextran with a molecular weight of 40000. 1-carboxypropyl-ortho-succinimide (1-cp-osu) is used as the linker. After producing PHEBA-1-cp-osu, this was coupled to the amino groups of the aminodextran by re-aminidation according to Anderson, G. W. et al., J. Amer. Chem. Soc. 86 (1964), 1839. In order to achieve a coupling of 1:10 (dextran: PHEBA), 400 mg aminodextran was dissolved in 40 ml 50 mM $KHPO_4$ buffer, pH 8.5 with 100 mM NaCl and 41.5 mg PHEBA-1-cp-osu in 4.15 ml dioxan was added dropwise. After a two hour reaction at room temperature it was stopped with 2 ml 0.1M lysine solution pH 8.5. The PHEBA(-1-cp-osu)-dextran was dialyzed three times against a 2000-fold volume in order to remove contaminants.

1.3 Precipitation test for the detection of phenobarbital

The following solutions were used:

Solution 1: (reaction buffer with dextran reagent)

200 µg/ml PHEBA(-1-cp-osu)-dextran with a coupling of 1:10

100 mM $KPO_4$, pH 7.4

4% polyethylene glycol (PEG) 40000

0.1% bovine serum albumin

1% Tween 20

0.1% $NaN_3$

Solution 2: (antiserum)

Polyclonal sheep-antibody crude serum against PHEBA was diluted 1:10 with 100 mM $KPO_4$, pH 7.4. The amount required per test was 5 µl crude serum. This corresponds to about 100 µg polyclonal antibody against PHEBA.

Solution 3: (sample)

Human serum which was supplemented with 0–80 µg PHEBA/ml was used as a standard. The measurement was carried out on a Hitachi 704 of the Boehringer Mannheim GmbH at a temperature of 30° C., a wavelength of 340 nm and a correction wavelength of 700 nm. 10 µl solution 3 (sample) was mixed with 350 µl solution 1 and incubated for 5 minutes. Afterwards the absorbance A1 was measured. 50 µl solution 2 was added by pipette and the test mixture was incubated for a further 5 minutes. Afterwards the second absorbance A2 was measured. In order to evaluate the results the absorbance difference A=A2−A1 was plotted on a graph against the PHEBA concentration. The results of the competitive detection of PHEBA are shown diagrammatically in FIG. 1.

EXAMPLE 2

Determination of glycosylated haemoglobin ($HbA_{1c}$)

In order to produce the multivalent dextran reagent with coupled $HbA_{1c}$, aminodextran (MW 40000) produced according to the description given in 1.1 was used as starting material. The glycosylated haemoglobin or a $HbA_{1c}$ analogue was coupled to maleimido-functionalized aminodextran via its sulfhydryl group according to Kitagawa et al., J. Biochem. 79 (1976), 233.

The fructosylated N-terminal tetrapeptide of the β chain of haemoglobin was used as the $HbA_{1c}$ analogue. The dextran-peptide conjugate (fruc-1-4-(cys, MHS)-dextran) was prepared with degrees of coupling of 1:14 and 1:28 (dextran:peptide). A peptide-bovine serum albumin conjugate (fruc-1-4(Cys, MHS)-BSA) with a degree of coupling of 1:18 was prepared in order to make a comparison with the state-of-the-art method.

In order to achieve a degree of coupling of 1:14 with dextran, 50 mg aminodextran was dissolved in 5 ml 50 mM $KPO_4$ buffer, pH 6.8 and a solution of 10 mg maleimidohexanoyl-N-hydroxy-succinimide ester (MHS) in 0.5 ml dioxan is added dropwise at room temperature while stirring. After a reaction time of two hours the reaction product is dialyzed against 5 liters 20 mM $KPO_4$ buffer, pH 7.0. A coupling of 1:14 is achieved under these conditions which is reproducible.

A solution of 137 mg $HbA_{1c}$-Cys-peptide in 1 ml 100 mM $KPO_4$ buffer, pH 6.8 is added at room temperature to 50 mg activated aminodextran in 2.5 ml $KPO_4$ buffer, pH 6.8. After a reaction time of two hours the preparation is separated chromatographically over ACA 202.

In order to achieve a coupling of 1:28, 400 mg aminodextran is dissolved in 20 ml 50 mM $KHPO_4$ buffer, pH 6.8 and reacted with 140 mg MHS in 12.3 ml dioxan according to the details given above.

480 mg activated aminodextran was incubated in 20 ml 100 mM $KHPO_4$ buffer, pH 6.8 for two hours at room temperature with a solution of 274 mg $HbA_{1c}$-Cys-peptide in 4.22 ml $KHPO_4$ buffer and the reaction product is separated chromatographically over ACA.

Bovine serum albumin was activated with MHS according to these instructions and the $HbA_{1c}$-cysteine peptide is coupled to this.

The precipitation test was carried out according to the instructions under 1.3 on a Hitachi 704 of the Boehringer Mannheim GmbH.

The following solutions were used:

Solution 1: (antiserum)

20 mM MES, pH 6.0

50 mM NaCl 0.5% detergent

3% PEG 6000

6.0 mg/ml PAB<$HbA_1$>-S-IgG (DE) or 5.0 mg/ml PAB<$HbA_{1c}$>-S-IgG (DE)

Solution 2: (dextran reagent)

20 mM MES, pH 6.0

150 mM NaCl 0.5% detergent 6.0% PEG 6000

25 µg/ml fruc-1-4(Cys, MHS)-dextran 1:14 or 20 µg/ml fruc-1-4(Cys, MHS)-dextran 1:28 or 25 mg/ml fruc-1-4(Cys, MHS)-BSA 1:18

Solution 3:

The calibration curve was established using haemolyzed and denatured EDTA-blood with a known $HbA_{1c}$ content which was appropriately diluted with haemolysis reagent. Known methods according to the state of the art were used for the haemolysis and denaturation.

Figure 2:
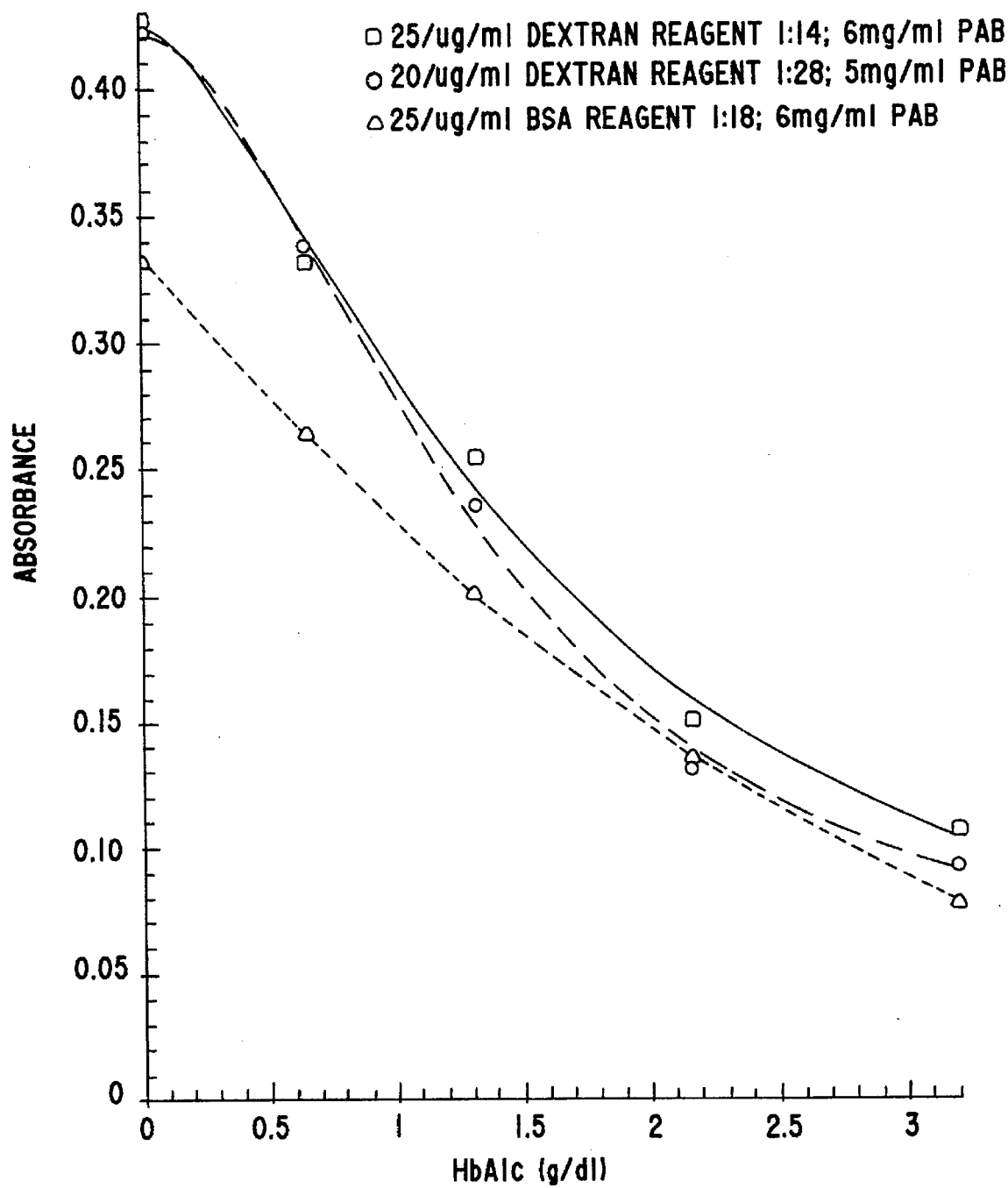
FIG. 2 shows the detection of glycosylated hemoglobin ($HbA_{1c}$).

250 µl solution 1 and 6 µl solution 3 were incubated for 5 minutes at 37° C. Afterwards the absorbance A1 was determined at 340 nm (correction wavelength 700 nm). The absorbance A2 was determined after the addition of 50 µl solution 2 and of a further 5 minutes incubation. The difference in absorbance A=A2−A1 was plotted on a graph against the $HbA_{1c}$ concentration (FIG. 2) for the evaluation. Using the dextran reagent according to the present invention it is possible to achieve a higher sensitivity independent of the degree of coupling than with a BSA reagent with a degree of coupling of 1:18 whereby a higher incorporation is not possible using BSA. When the dextran reagent is used with a degree of coupling of 1:28 the use of less PAB and dextran reagent already leads to the same calibration curve as the dextran reagent with the lower degree of coupling. The use of larger concentrations ($C_{PAB}$=6 mg/ml; $C_{dextran\ reagent}$=25 µg/ml) with the dextran reagent of 1:28 leads to a further increase in the sensitivity of the competitive immunoassay.

Figure 3:
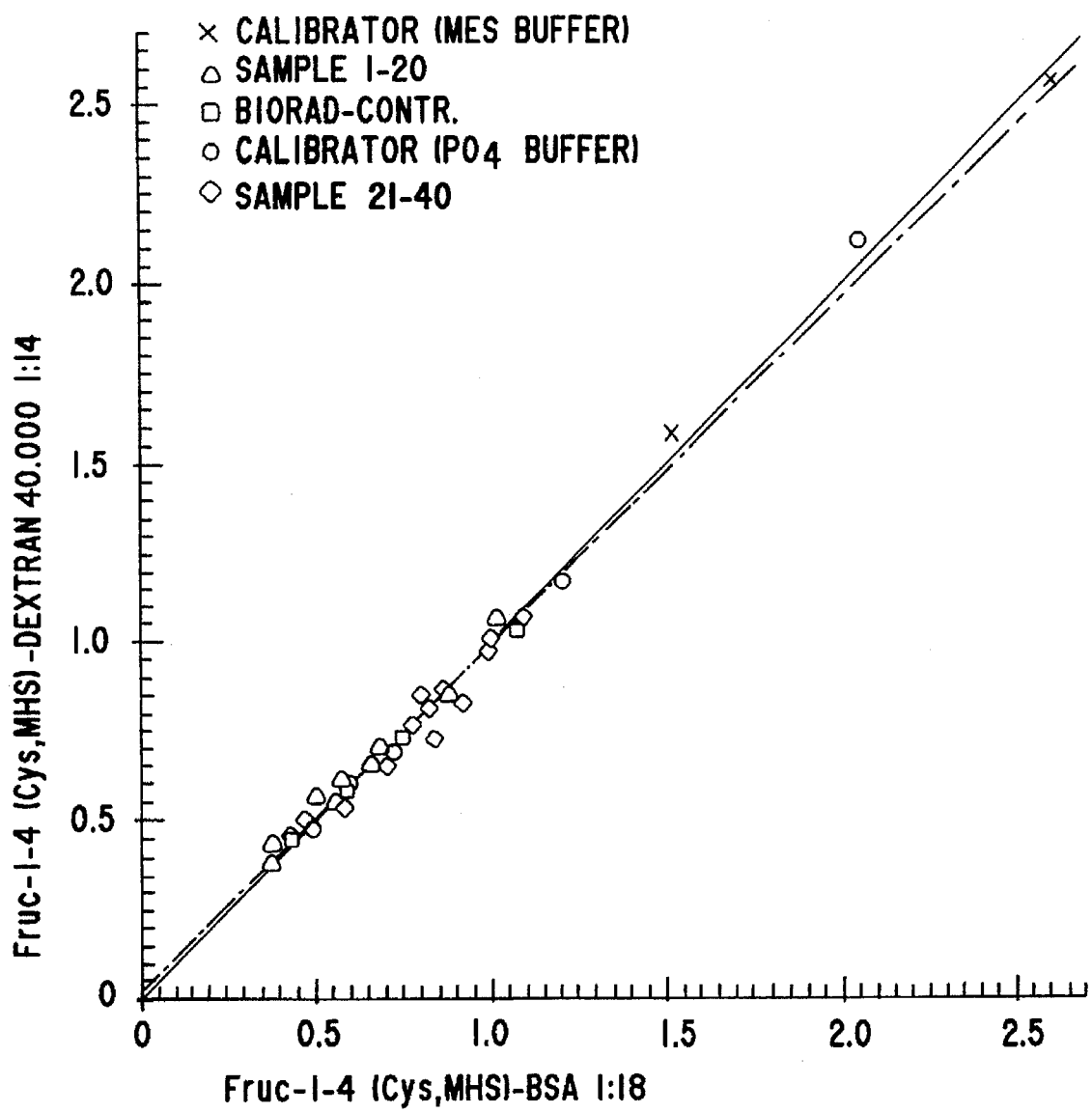
FIG. 3 compares the method of the present invention ($HbA_{1c}$) and the method of the state of the art.

Very good correlations (correlation coefficient 0.995) between the method according to the present invention and the method of the state of the art were seen in the method comparison (FIG. 3).

We claim:

1. A nephelometric or turbidimetric method for determining a specifically bindable substance, which substance is bivalent or polyvalent, comprising providing a reaction mixture by reacting a test sample suspected for containing the specifically bindable substance with a precipitation reagent comprising a solution of multivalent dextran reagent comprising soluble dextran of molecular weight 10,000 to about 2 million, having a plurality of receptors R1 covalently bound thereto, where said R1 specifically binds to any of the specifically bindable substance in the test sample to form a precipitate which remains in solution in said reaction mixture, measuring the extent of precipitation in said reaction mixture by nephelometric or turbidimetric measurement means to determine the amount of the specifically bindable substance present in the test sample.

2. The method according claim 1, wherein said plurality of the receptor R1 are bound to the soluble dextran via two receptors R3 and R4, whereby the R3 is covalently bound to the soluble dextran and specifically binds to the receptor R4, wherein said R4 is covalently bound to the receptor R1.

3. The method according to claim 2 wherein the specific binding of the two receptor R3 and R4 takes place in said reaction mixture.

4. The method according to claim 1, further comprising adding one or more reagents selected from the group consisting of buffers, reaction accelerators, substances which reduce interference and detergents to the reaction mixture.

5. A nephelometric or turbidimetric method for determining a specifically bindable substance which substance is monovalent, comprising providing a reaction mixture by reacting a test sample suspected for containing the specifically bindable substance with a precipitation reagent comprising a solution of multivalent dextran reagent comprising soluble dextran of molecular weight 10,000 to about 2 million, having a plurality of molecules of the specifically bindable substance or an analogue of the specifically bindable substance covalently bound thereto, further reacting a receptor R2 which is at least bivalent, wherein said R2 specifically binds any specifically bindable substance in the test sample and the analogue to form a precipitate which remains in solution in said reaction mixture, measuring the extent of precipitation in said reaction mixture by nephelometric or turbidimetric measurement means to determine the amount of the specifically bindable substance present in the test sample.

6. The method according to claim 5, wherein said R2 is an antibody or a bivalent antibody fragment.

7. The method according to claim 5, further comprising adding one or more reagents selected from the group consisting of buffers, reaction accelerators, substances which reduce interference, and detergents to the reaction mixture.

8. The method according to claim 5, wherein said plurality of molecules of the specifically bindable substance or the analogue of the specifically bindable substance are bound to the soluble dextran-an via two receptors R3 and R4, whereby the R3 is covalently bound to the soluble dextran and specifically binds to the receptor R4, wherein said R4 is covalently bound to the specifically bindable substance or the analogue of the specifically bindable substance.

9. The method according to claim 8 wherein the specific binding of the two receptors R3 and R4 takes place in said reaction mixture.

10. The method according to claim 5 wherein the receptor R2 is covalent bound to a second multivalent dextran reagent comprising a soluble dextran of molecular weight 10,000 to about 2 million.

* * * * *